(12) United States Patent
Contreras et al.

(10) Patent No.: US 9,010,148 B2
(45) Date of Patent: Apr. 21, 2015

(54) METHOD OF REDUCING DISTORTION IN A SHEET OF GLASS

(75) Inventors: Cynthia C. Contreras, Kettering, OH (US); Edward A. Cuellar, Canandaigua, NY (US); Shawn R. Markham, Harrodsburg, KY (US)

(73) Assignee: Corning Incorporated, Corning, NY (US)

( * ) Notice: Subject to any disclaimer, the term of this patent is extended or adjusted under 35 U.S.C. 154(b) by 420 days.

(21) Appl. No.: 13/485,301

(22) Filed: May 31, 2012

(65) Prior Publication Data

US 2013/0319047 A1 Dec. 5, 2013

(51) Int. Cl.
 G01N 33/38 (2006.01)
 G01N 21/23 (2006.01)
 G01N 21/896 (2006.01)

(52) U.S. Cl.
 CPC .............. *G01N 33/386* (2013.01); *G01N 21/23* (2013.01); *G01N 21/896* (2013.01)

(58) Field of Classification Search
 CPC .... C03B 17/06; C03B 17/064; C03B 17/067; G01N 21/23; G01N 33/386
 USPC ........... 65/29.1, 29.12, 29.18, 53, 90, 195, 97
 See application file for complete search history.

(56) References Cited

U.S. PATENT DOCUMENTS

| | | | |
|---|---|---|---|
| 3,909,226 A * | 9/1975 | McCourty et al. ................. | 65/97 |
| 5,654,057 A | 8/1997 | Kitayama et al. ............ | 428/64.1 |
| 6,451,043 B1 | 9/2002 | McInnes et al. ............... | 606/194 |
| 6,758,064 B1 | 7/2004 | Kariya ................................. | 65/91 |
| 7,685,840 B2 * | 3/2010 | Allaire et al. ................. | 65/29.12 |
| 7,984,625 B2 * | 7/2011 | Markham et al. ............. | 65/29.12 |
| 8,141,388 B2 | 3/2012 | Burdette ........................... | 65/90 |
| 8,210,001 B2 * | 7/2012 | Allan et al. ........................ | 65/53 |
| 2005/0120748 A1* | 6/2005 | Xun et al. ......................... | 65/53 |
| 2008/0066498 A1* | 3/2008 | Markham et al. ............. | 65/29.16 |
| 2010/0043495 A1* | 2/2010 | Kirby et al. ...................... | 65/91 |
| 2011/0075140 A1 | 3/2011 | Adriaansen et al. ........ | 356/239.1 |
| 2011/0165380 A1 | 7/2011 | Gahagan et al. .............. | 428/156 |
| 2012/0111055 A1* | 5/2012 | Allan et al. ................... | 65/29.18 |

FOREIGN PATENT DOCUMENTS

WO 2005/055284 6/2005

OTHER PUBLICATIONS

PCT/US2013/043574 Search Report.

* cited by examiner

*Primary Examiner* — Jason L Lazorcik
(74) *Attorney, Agent, or Firm* — Kevin M. Able

(57) ABSTRACT

A method of reducing distortion in a glass sheet is described and comprises the steps of: forming a glass ribbon in a glass manufacturing process; separating a glass sheet from the glass ribbon, the glass sheet having a substantially flat surface; measuring a retardation through the surface of the glass sheet; defining a retardation parameter indicative of the retardation of the glass sheet; cutting the glass sheet into a plurality of sub-sheets; measuring a distortion of the sub-sheets; defining a distortion parameter indicative of the distortion of the sub-sheets; and determining a correlation between the retardation parameter and the distortion parameter such that the distortion parameter of sub-sheets of a subsequent glass sheet can be predicted based on the correlation.

18 Claims, 3 Drawing Sheets

METHOD OF REDUCING DISTORTION IN A SHEET OF GLASS

TECHNICAL FIELD

The present disclosure relates generally to glass substrates and more particularly to a glass substrate product for use in display manufacturing processes.

BACKGROUND

The physical dimensions of a glass substrate used in the production of a liquid crystal display (LCD) device allow only small room for error because misalignment of components in the device can lead to visually detectable defects that result in a product that is unacceptable to the consumer.

One factor that can cause such a defect is stress that is frozen into the glass sheets during manufacture of a parent glass sheet and that result in distortion of the sub-sheets cut from the parent glass sheet. This distortion is exacerbated as the size of the sheet is increased. However, such future distortion is not easily discerned in the parent glass sheet as manufactured by the glass manufacturer.

Thus, there is a need for a method of determining and reducing distortion which may be exhibited by sub-sheets from stresses present within the parent glass sheet.

SUMMARY

In one example aspect, a method of reducing distortion in a glass sheet is provided. The method comprises the steps of forming a glass ribbon in a glass manufacturing process; separating a glass sheet from the glass ribbon, the glass sheet having a substantially flat surface; measuring a retardation through the surface of the glass sheet; defining a retardation parameter indicative of the retardation of the glass sheet; cutting the glass sheet into a plurality of sub-sheets; measuring a distortion of the sub-sheets; defining a distortion parameter indicative of the distortion of the sub-sheets; determining a correlation between the retardation parameter and the distortion parameter such that the distortion parameter of sub-sheets of a subsequent glass sheet can be predicted based on the correlation; and modifying the glass manufacturing process such that the retardation of the subsequent glass sheet is adjusted to thereby reduce the distortion of the sub-sheets from the subsequent glass sheet based on the correlation.

In one example of the example aspect, the distortion parameter is kept below a specific value with a predetermined probability.

In another example of the example aspect, the step of measuring the distortion of the sub-sheets involves measuring an in-plane distortion defined as an offset of a first set of points along a plane of the sub-sheets prior to and after the step of cutting.

In yet another example of the example aspect, the distortion parameter is equal to a maximum of the in-plane distortion measured at the first set of points.

In yet another example of the example aspect, the step of measuring the retardation includes measuring the retardation at a second set of points on the surface and the retardation parameter is an average of the retardation at the second set of points.

In another example aspect, a method of reducing distortion in a glass sheet is provided. The method comprises the steps of: forming a glass ribbon in a glass manufacturing process; separating a glass sheet from the glass ribbon, the glass sheet having a substantially flat surface; measuring a retardation through the surface of the glass sheet; defining a retardation parameter indicative of the retardation of the glass sheet; cutting the glass sheet into a plurality of sub-sheets; measuring a distortion of the sub-sheets; defining a distortion parameter indicative of the distortion of the sub-sheets; and determining a correlation between the retardation parameter and the distortion parameter such that the distortion parameter of sub-sheets of a subsequent glass sheet can be predicted based on the correlation.

In one example of the another example aspect, the method further comprises a step of predicting the distortion parameter of sub-sheets of a subsequent glass sheet using the correlation between the retardation parameter and the distortion parameter.

In another example of the another example aspect, the method further comprises a step of modifying the glass manufacturing process such that the retardation of the subsequent glass sheet is adjusted to thereby reduce the distortion of the sub-sheets from the subsequent glass sheet based on the correlation.

In yet another example of the another example aspect, the distortion parameter is kept below a specific value with a predetermined probability.

In yet another example of the another example aspect, the method further comprises a step of flattening the glass sheet before the step of measuring the retardation; and the step of flattening each of the sub-sheets before the step of measuring the distortion.

In yet another example of the another example aspect, the step of determining involves formulating an equation using a least squares regression approach.

In yet another example of the another example aspect, the step of measuring the distortion of the sub-sheets involves measuring an in-plane distortion defined as an offset of a point along a plane of the sub-sheets prior to and after the step of cutting.

In yet another example of the another example aspect, the step of measuring the in-plane distortion of the sub-sheets involves measuring the in-plane distortion of a first set of points on the sub-sheets.

In yet another example of the another example aspect, the distortion parameter is equal to a maximum of the in-plane distortion measured at the first set of points.

In yet another example of the another example aspect, the method further comprises a step of modifying the glass manufacturing process such that the retardation of the subsequent glass sheet is adjusted to thereby reduce the distortion of the sub-sheets from the subsequent glass sheet based on the correlation, and the maximum of the in-plane distortion is kept below a specific value with a predetermined probability.

In yet another example of the another example aspect, the distortion parameter is equal to an average of the in-plane distortion measured at the first set of points.

In yet another example of the another example aspect, the method further comprises a step of modifying the glass manufacturing process such that the retardation of the subsequent glass sheet is adjusted to thereby reduce the distortion of the sub-sheets from the subsequent glass sheet based on the correlation, and the average of the in-plane distortion is kept below a specific value with a predetermined probability.

In yet another example of the another example aspect, corners of the sub-sheets define the first set of points.

In yet another example of the another example aspect, the point is a centroid of each of the sub-sheets.

In yet another example of the another example aspect, the method further comprises a step of measuring the retardation includes measuring the retardation at a second set of points on the surface and the retardation parameter is an average of the retardation at the second set of points.

BRIEF DESCRIPTION OF THE DRAWINGS

These and other aspects are better understood when the following detailed description is read with reference to the accompanying drawings, in which.

DETAILED DESCRIPTION

Figure 1:
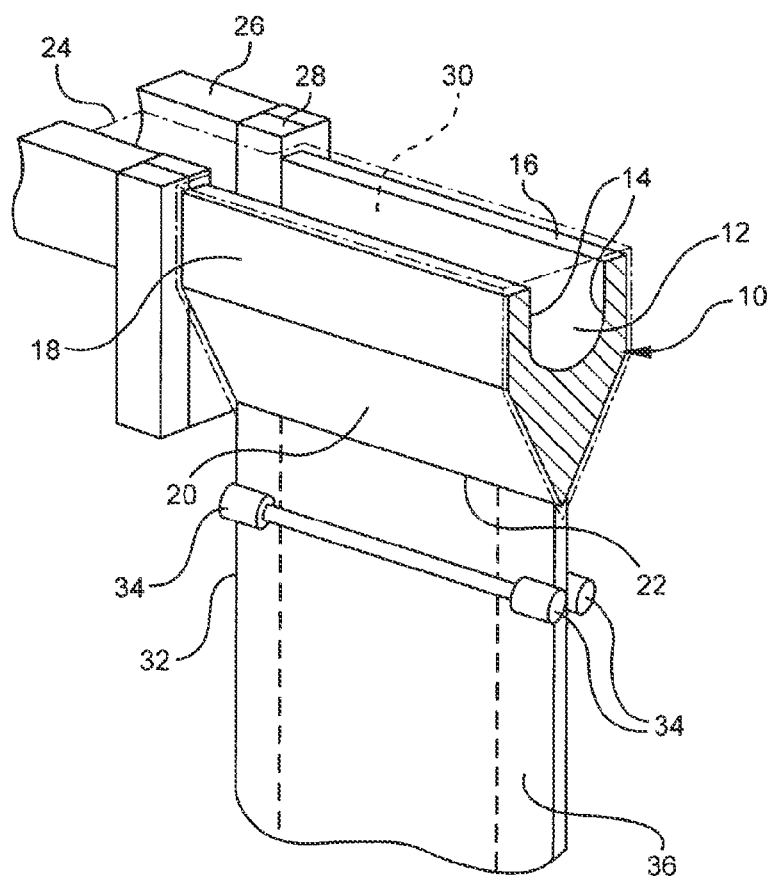
FIG. 1 is a perspective view of a fusion downdraw glass making apparatus.

Examples will now be described more fully hereinafter with reference to the accompanying drawings in which example embodiments are shown. Whenever possible, the same reference numerals are used throughout the drawings to refer to the same or like parts. However, aspects may be embodied in many different forms and should not be construed as limited to the embodiments set forth herein.

As used herein, a downdraw glass sheet manufacturing process refers to any form of glass sheet manufacturing processes in which glass sheets are formed while viscous glass is drawn in a downward direction. Particularly, in a fusion downdraw glass forming process, molten glass flows into a trough, then overflows and runs down both sides of a pipe or forming wedge, more commonly referred to as an isopipe. The two flows fuse together at what is known as the root (where the pipe ends and the two overflow portions of glass rejoin), and the combined flow is drawn downward until cool.

The fusion overflow glass sheet manufacturing process can be described with the help of an embodiment illustrated in FIG. 1, wherein forming wedge 10 includes an upwardly open channel 12 bounded on its longitudinal sides by wall portions 14, which terminate at their upper extent in opposed longitudinally-extending overflow lips or weirs 16. The weirs 16 communicate with opposed outer sheet forming surfaces of forming wedge 10. As shown, forming wedge 10 is provided with a pair of substantially vertical forming surface portions 18 which communicate with weirs 16, and a pair of downwardly inclined and converging surface portions 20 which terminate at a substantially horizontal lower apex or root 22 forming a straight, glass draw line.

Molten glass 24 is fed into channel 12 by means of delivery passage 26 communicating with channel 12. The feed into channel 12 may be single ended or, if desired, double ended. A pair of restricting dams 28 are provided above overflow weirs 16 adjacent each end of channel 12 to direct the overflow of the free surface 30 of molten glass 24 over overflow weirs 16 as separate streams, and down opposed forming surface portions 18, 20 to root 22 where the separate streams, shown in chain lines, converge to form a ribbon of virgin-surfaced glass 32 from which sheets of glass can be separated and further processed.

In the fusion process, a pulling device in the form of pulling rolls or rollers 34 are placed downstream of forming wedge root 22 and are used to adjust the rate at which the formed ribbon of glass leaves the converging forming surfaces at the root and thus help determine the nominal thickness of the finished sheet. The pulling rolls are typically designed to contact the glass ribbon at its outer edges portions 36 only, leaving the interior, quality region of the glass ribbon untouched. The ribbon is thereafter cut into individual glass sheets and edge portions 36 which have been contacted by the pulling rolls are discarded from the sheet, leaving only quality surfaces.

One advantage to the fusion glass forming process described above is that the ribbon can be formed without the glass ribbon quality surfaces contacting the forming apparatus surfaces, such as the pulling rolls, while the viscosity of the glass is low enough as to not sustain plastic deformation or damage. This provides for smooth, contaminant-free glass surfaces. In addition, this technique is capable of forming very flat and thin glass sheets to very high tolerances. However, other glass sheet forming techniques may also benefit from the present disclosure, including, but not limited to, single-sided overflow downdraw, slot draw, updraw and float forming techniques.

The stresses which may be present in a formed article of glass are highly dependent upon the manufacturing process used, and the thermal history of the glass. This is just as true for glass sheet as for other glass articles. Many times the stresses which may be frozen into the finished glass sheet are the result of thermal gradients experienced by the glass ribbon from which the sheet is cut as the glass of the ribbon transitions from a viscous liquid to a glassy solid state. They may also enter the glass through mechanical deformation of the glass during this transition. Regardless the source, these stresses are distributed within the finished sheet, by manufacturing design, such that the finished sheet as provided to the original equipment manufacturer (OEM) is substantially planar with substantially parallel opposing edges. This is due in large part to the care taken by the manufacturer during the manufacturing process, as attempts are generally made to either eliminate stress within the sheet, or to create counter-balancing stresses within the sheet to mitigate sources of stress which are known, but not easily eliminated. Thus, the substantially planar sheet of glass produced by the glass manufacturer exhibits minimal distortion. However, this may change when the glass sheet is further processed, for example, by a display manufacturer or other OEM. As described previously, the OEM is faced with the task of first depositing electrical components for a display device on glass substrates, and then aligning two (or more) substrates, such that the components on one substrate align precisely with the components on the other substrate(s). Once optimally aligned, the substrates may be sealed to form a display device.

An OEM manufacturing process may often require that large glass sheets purchased from the glass manufacturer be cut into sections, or sub-sheets, for optimum material utilization or handling ability. These sub-sheets can serve as display device substrates. The size of the sub-sheets depends, inter alia, on the particular type of display being manufactured. However, generally the sub-sheets are rectangular, with parallel opposing edges. It is when the parent glass sheet is cut into sub-sheets that stress-related distortion may impact the OEM manufacturing process. Cutting the glass sheet may result in a redistribution of stress such that the stresses in the sub-sheets reach a new equilibrium. This equilibrium is generally reached by a shape change—distortion—of the sub-sheets.

Distortion of the sub-sheets cut from a parent glass sheet may be three-dimensional. That is, the sheet may exhibit both warping transverse to the plane of the parent sheet, and planar distortion. During processing however, OEMs typically flatten the glass sub-sheets, such as by using a vacuum platen. Thus, distortion experienced by the OEM is artificially constrained to in-plane distortion can thus be defined as an offset by which a point (e.g., a corner of a sub-sheet) moves along a plane in which the sub-sheet lies before the sub-sheet is cut from the parent sheet and after the sub-sheet is cut. Once a sheet of glass is cut, the in-plane shape of the sheet may change, e.g. opposing edges of the sub-sheets may no longer be parallel. In order for the glass manufacturer to predict distortion in cut sub-sheets, it is therefore desirable that OEM processes be mimicked as much as possible by conducting distortion measurements on glass sheets which have been similarly constrained.

Since an offset of only 2% between corresponding components on substrates to be joined (sealed) is a problem, and that such individual components can be on the scale of micrometers in size, it can be easily seen that even minute distortion can be troublesome to a display OEM. The present disclosure provides a methodology for reducing distortion in post-forming processes by predicting in-plane distortion in a sheet of glass, and feeding the resultant information back into the glass manufacturing process to reduce the predicted distortion, and therefore also the actual sub-sheet distortion experienced in downstream, post-forming processing such as those performed by OEMs.

As suggested previously, glass manufacturers form glass sheets for display applications to be flat, and preferably with parallel opposing edges. However, the dimensional tolerances within the glass manufacturing process per se do not typically extend into the micron range. Moreover, as the distortion phenomenon which is the subject of the present disclosure can be measured only after the parent glass sheet is cut, the detection process itself is destructive, and obviates the OEMs desire for receiving large sheets of glass. To wit, direct detection of distortion which may occur at a future date only after the parent glass sheet has been cut is not possible at the glass manufacturing stage. However, stresses within the glass can be more easily measured, and particularly those stresses at the edges of the glass sheet. And these stresses may be used to predict distortion in sub-sheets cut from the parent glass sheet.

Figure 2:
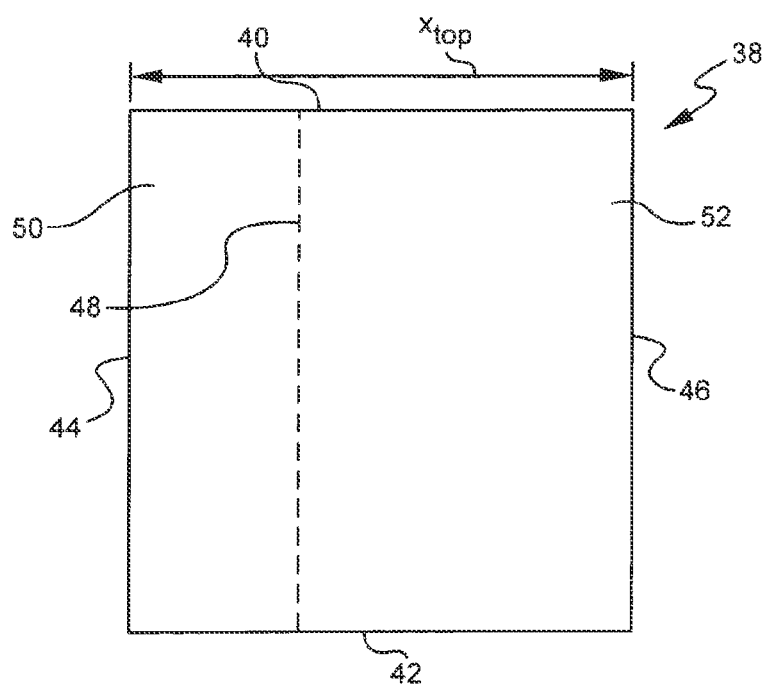
FIG. 2 is a top view of a sheet of glass indicated with a line along which the glass sheet may be cut into a several sub-sheets in accordance with an example method.

An exemplary parent glass sheet 38 for the manufacture of a display device is shown in FIG. 2. Also shown is each edge segment of sheet 38: top edge segment 40; bottom edge segment 42, first side edge segment 44, and; second side edge segment 46. A cut line 48 is depicted and represents a location where an OEM might cut parent sheet 38 into manageable sizes, e.g. therefore forming two sub-sheets 50, 52. Of course, the OEM may divide the sheet in a variety of different ways, producing any number of sub-sheets depending upon the application, and the division of parent glass sheet 38 into a minimal two sub-sheets is merely for purposes of illustration.

Figure 3:
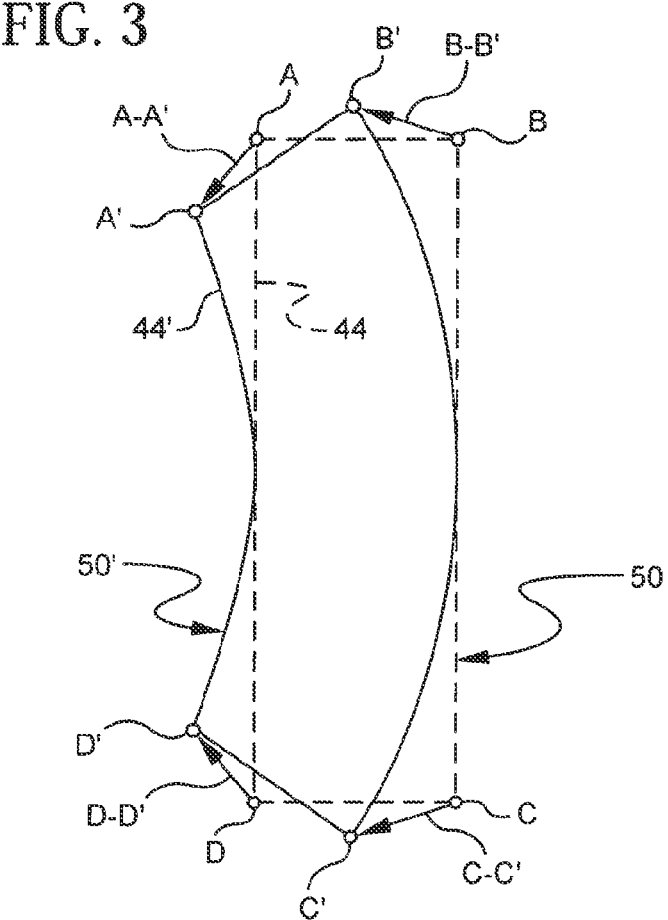
FIG. 3 is a top view of a sub-sheet of FIG. 2 which is distorted by the stress relaxation after cutting, overlaid on an outline of the same sub-sheet had there been no distortion.

FIG. 3 shows a sub-sheet, formed after cutting parent glass sheet 38, overlaid on the outline of the sub-sheet as if there had been no distortion. In FIG. 3, the undistorted outline of sub-sheet 50 is indicated by a dashed line, and reference numeral 50, in keeping with the designation shown in FIG. 2, and the actual, distorted sub-sheet after the cutting is denoted by a solid line and reference numeral 50'. As depicted, sub-sheet 50' exhibits at least an in-plane curvature (exaggerated in the figure) after being cut from parent glass sheet 38. Of course, sub-sheet 50' could have assumed a variety of different shapes, such as barrel distortion for example. However, the curved, in-plane distortion shown in FIG. 3 will be used to describe the present disclosure, without limitation to the actual shape a sub-sheet may assume after being cut from the parent sheet.

As one might expect, aligning display components on two sub-sheets which exhibit distortion may prove problematic, particularly if the shapes of the two sub-sheets are different. The distortion exhibited by sub-sheet 50' may be represented, for example, by the distance between a pre-determined point on sub-sheet 50, and the corresponding actual position of that point on cut sub-sheet 50' due to distortion in the cut sub-sheet. For the sake of illustration, one might select one or more corner points of the sub-sheet, and measure the distance from where the corner points should be (or are desired to be) after cutting to where the corners actually are after cutting. Thus, in one embodiment, distortion in sub-sheet 50' may be represented by the vector distance (or offset) between points A and A', B and B', C and C' and D and D'. This offset represents distortion. Of course, repositioning the cut sub-sheet in precisely the same position it occupied when it was a part of the parent glass sheet would be difficult enough if no distortion was present. In the case where the sub-sheet distorts due to the cutting, it is desirable to place the sub-sheet in a position after cutting which reduces the offset so that an accurate reflection of the distortion can be obtained.

Figure 4:
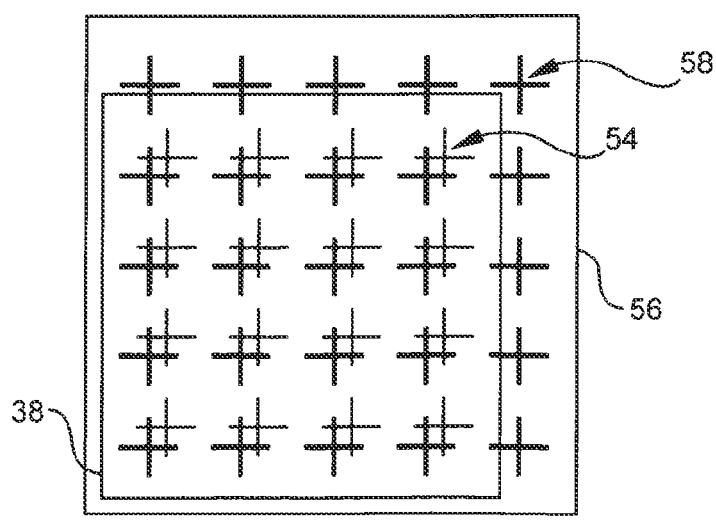
FIG. 4 is a top view of a measurement table having fiduciary marks, and a glass sheet having corresponding fiduciary marks resting on the measurement table.
Figure 5:
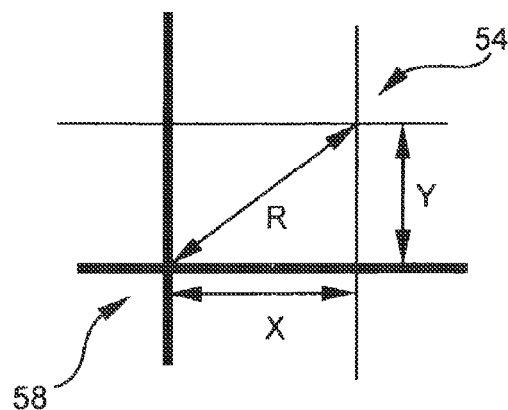
FIG. 5 illustrates a method of representing an offset between the table and sheet fiduciary marks of FIG. 4.

In one example embodiment, a parent sheet 38 marked with indicia in the form of fiduciary marks 54 (such as an array of x's) may be positioned on a planar measurement table 56 having corresponding fiduciary marks 58 such that the fiduciary marks 54 of parent glass sheet 38 are offset (linearly translated) from the table fiduciary marks 58, as is shown in FIG. 4. It is desirable that measurement table 56 have similar thermal expansion properties to glass sheet 38 being measured. Parent glass sheet 38 is positioned on the table such that the parent glass sheet fiduciary marks 54 are offset slightly in the x and y directions from the measurement table fiduciary marks 58. The parent glass sheet and the measurement table are then imaged with a high resolution imaging system (not shown) and the image (or images) analyzed to quantify the X and Y offsets, e.g. the line spacing in the example shown in FIG. 5 represented by a distance in the x-direction and a distance in the y-direction and R represents the direct distance between the two fiduciary marks. Next, parent glass sheet 38 is cut, producing a plurality of sub-sheets. Each sub-sheet is replaced on the table, re-imaged and the offset between table and sub-sheet fiduciary marks mathematically reduced. Also, as previously described, it is desirable to constrain the distortion exhibited by the sub-sheet to an in-plane distortion by flattening the sub-sheet. Again, this may be easily accomplished, for example, if the measurement table is in the form of a vacuum platen. Since the sub-sheet is constrained to be substantially planar, the offset of each fiduciary mark on the sub-sheet from the table fiduciary marks can be broken down into simple translational and rotational components and a conventional coordinate system transformation used to reduce the offset. Such computational reduction may be accomplished with the assistance of a computer. Simple spreadsheet computations may suffice. Of course, other methods of marking and measuring position and positional changes as are known in the art may be used as well.

Distortion of sub-sheet 50' may be further represented by selecting, calculating or otherwise determining a distortion parameter that is indicative of the distortion of the sub-sheet. For example, the largest of the measured offsets between the aforementioned points may be selected as a distortion parameter. Thus, for example, in a sub-sheet wherein the A-A' displacement is 0.1 µm, the B-B' displacement is 0.25 µm, the C-C' displacement is 0.15 µm and the D-D' displacement is 0.075 µm, the sub-sheet may be said to exhibit 0.25 µm of in-plane distortion, corresponding to the largest displacement—between B and B'. It should be noted that individual OEMs may apply their own definition of distortion, and this should be accounted for during development of a predicted distortion model. That is, the method just described involving distortion relative to the corners of the sub-sheet, and selecting the maximum, is but one method of defining distortion according to the present embodiment. One could just as easily define the distortion as the displacement of the sub-sheet centroid, or the displacement of any other point or series of points on the sub-sheet. For example, OEMs may deposit components from multiple display devices on a sub-sheet, and the definition of distortion applied by the OEM may take this into account by applying a more refined definition, such as one having greater distortion resolution. This might occur by simply increasing the number of point-to-point paired offset distances computed. The distortion may also be represented not by selecting a maximum of measured distortion, but by calculating a distortion value from the individual measured distortions. For example, the distortion parameter of the sub-sheet may be the average of the individual measured distortions. The appropriate distortion representation for the sub-sheets depends largely on the needs of an individual OEM.

To align substrates (e.g. sub-sheets) with opposing, and corresponding display components for one or more display devices, OEMs typically employ an optimization routine, such as described above, to reduce the component offset when substrates are joined. Such optimization routines are generally proprietary to a particular OEM.

Based on the description supra, one can easily see how the allowable distortion in a glass sub-sheet sheet becomes an important consideration in the parent glass sheet manufacturing process. It should be equally clear that direct measurement of the future distortion of a glass panel cut by an OEM poses a fundamental dilemma to the glass manufacturer.

Glass sheets under nonisotropic stress are birefringent. Birefringent materials have two orthogonal optical axes with different refractive indices. Light polarized parallel to one axis travels through the material at a different speed than light polarized parallel to the orthogonal axis. This results in a phase shift between these two light components referred to as retardation. The retardation can, in turn, be used to calculate stress. These calculated stresses may then be used in further calculations to predict distortion in sub-sheets cut from the parent sheet. Analytical techniques or finite element analysis may be needed to determine stresses in the center of a sheet and the results are often sensitive to small changes in the underlying assumptions.

The usefulness of stress as a predictor of glass sub-sheet distortion, and particularly stress at the edges of the glass sheet, can decrease as the dimensions of the glass sheet increase, as edge stress becomes less representative of the stresses in the central regions of the parent glass sheet (and thus the sub-sheets cut therefrom) as the overall sheet size becomes larger. Moreover, as the size of the parent glass sheet becomes larger, the error in the calculated stress can be as large or larger than the allowable maximum distortion. On the other hand, the measured retardation values themselves can be performed with more certainty. Accordingly, retardation itself can be a better predictor of glass sub-sheet distortion than using an intermediate calculated stress for parent glass sheets having dimensions equal to or larger than about 1200 mm×1300 mm, and even more so for parent glass sheets equal to or larger than about 1500 mm×1800 mm.

In accordance with an embodiment of the present disclosure, retardation is measured at individual points arranged in a two-dimensional grid pattern across the entire surface of parent glass sheet 38 which is substantially flat. The retardation data is then analyzed in a manner consistent with the following description. By "consistent with", what is meant is that the analysis itself may be conducted computationally by a computing device (e.g. desktop computer, etc.).

Since retardation may not be identical across the surface of the parent sheet, it may be possible to devise a retardation parameter that is indicative of the retardation values measured on the parent sheet. The average retardation value $R_{av}$ of parent glass sheet 38 is determined as the simple arithmetic average of all the individual retardation measurements made on the glass sheet. The parent glass sheet 38 is then cut into sub-sheets and a plurality of distortions are measured for each sub-sheet. For example, the maximum corner offset, as previously described, may be chosen. However, because distortion is a function of the pattern of cut (e.g. the size of the sub-sheets), if the predicted distortion of glass sheets formed from the glass forming apparatus used will ultimately be used by a purchaser (e.g. OEM), the sheet must be cut in accordance with the manner in which a particular OEM cuts the glass, and the distortion (e.g. offset) calculated in the manner the OEM calculates the distortion. This may in turn be dependent upon the use to which the OEM puts the glass. For example, many OEMs deposit components for multiple displays on a single sub-sheet, and therefore may choose to measure distortion as a function of offset relative to the corners of each display component area as arranged on the sub-sheet rather than the corners of the sub-sheet itself. In any event, once the parent glass sheet is cut, a plurality of distortion measurements are made comprising the offset between a point on the parent glass sheet before the cut, and on the same point on the respective sub-sheet after the cut and a least one of the sub-sheet distortion measurements (i.e. offsets) used determined a representative offset for the sub-sheet. This is done for each sub-sheet.

The distortion parameter for each sub-sheet may be determined, for example, as the maximum measured distortion, or the distortion parameter may be some other value derived from the measured distortions, such as the average of the measured distortions. In most cases, the maximum of the measured distortions for a given sub-sheet is chosen, as this worst-case choice provides greater protection for the manufacturer in meeting a distortion specification.

Once a distortion parameter has been determined for each sub-sheet, a distortion representative of the collection of sub-sheets as a whole is determined and designated as the distortion parameter $\delta_{meas}$ of the parent sheet. As in the case of each sub-sheet, the distortion parameter for the collection of sub-sheets may be determined in a variety of ways. However, generally the distortion representative of the collection of sub-sheets (e.g. all of the sub-sheets cut from the parent glass sheet) is determined as the largest (maximum) of the distortion parameters for each individual sub-sheet.

The average retardation $R_{av}$ and absolute value of the distortion parameter $\delta_{meas}$ of n parent sheets constituting a single product are correlated using equation:

$$|\delta_{meas}|=M \cdot R_{av}+B \tag{1}$$

The correlation coefficient M is determined by conducting an ordinary least squares regression with intercept B.

Once formulated, equation (1) can be used to predict the amount of distortion sub-sheets of pre-determined size and shape will exhibit when cut from a given parent glass sheet. In this instance, $R_{av}$ is determined in accordance with the description based on the average retardation data for a given parent sheet of glass, and a value for the absolute value of maximum distortion calculated in place of the measured distortion value. That is, $\delta_{meas}$ is replaced with $\delta p_{Pmax}$ in equation (1). In effect, one may then, for example, calculate and assign a maximum predicted distortion value to the parent glass sheet, effectively describing the maximum distortion which could be expected to be exhibited by a sub-sheet cut from the parent sheet.

As described, the definition of the distortion, i.e. how distortion is measured, may be determined by a particular OEM, or selected by the glass manufacturer. Glass sheet manufactured subsequent to the sheet of glass analyzed in accordance with the method described supra, and drawn from the same forming apparatus, may be measured for retardation and the analysis in accordance with the present embodiment applied to determine a predicted distortion for subsequent parent glass sheets using the coefficient M and intercept B obtained during the previous analysis. The manufacturing process may then be modified in response to the predicted distortion. For example, the glass ribbon drawn from a fusion apparatus as described herein may be subjected to a pre-determined cooling scheme wherein the temperature of the glass ribbon (from which the parent glass sheet is cut) is varied as a function of the temperature (or viscosity) of the glass and/or the location across the width of the ribbon.

The glass making and forming processes may be modified to reduce the predicted distortion, if necessary, such as by varying the cooling and/or heating scheme of the glass ribbon as it is drawn. Other process variables which may be modified according to known methods in response to the predicted distortion include, but are not limited to, sheet draw or pulling rate, draw tension, and isopipe/glass temperature.

To ensure a more accurate prediction of distortion, the preceding retardation analysis may be performed for a plurality of parent glass sheets over a given period of time in order to capture the effects of inevitable process variation. Thus, for example, one might perform the analysis in accordance with the present disclosure on multiple parent glass sheets on a daily basis over a period of several days or weeks. The results of these multiple measurements may then be combined and equation (1) refit.

It should be obvious to one skilled in the art from the disclosure herein that the average retardation value may be used as a manufacturing control parameter for distortion in a manner as is known in the art. Thus, control limits are placed on the average retardation value and the glass sheet manufacturing process controlled within those limits so as not to exceed the manufacturing limit for distortion by a pre-determined amount.

The average retardation value may further be used as a product specification in the trade and commerce of glass sheet between OEMs and glass manufacturers. In this instance, the predicted maximum distortion for a given parent glass sheet for a given value of the average retardation for that parent glass sheet is compared to a pre-determined value of maximum distortion as a pass/fail criteria against the sheet. For example, the pre-determined pass/fail criteria may be set at $\delta_{Pmax} \leq 1.5$ μm. Alternatively, it may be necessary that the distortion in sub-sheets of glass cut from a parent glass to be as low as 0.7 μm on average and less than 1.0 μm on an individual basis. Statistical sampling methods as are known in the art may be applied such that the population of glass sheets may be sampled rather than each individual glass sheet measured for average retardation to determine performance against the pass/fail limit.

The following shows one example of correlating the average retardation to the distortion. This example illustrates the use of ordinary least squares regression to correlate average retardation of each glass sheet of a sample glass sheets from a run of fusion-drawn glass to the absolute value of the maximum distortion of four sub-sheets cut from each parent sheet in the sample.

Each parent sheet was 1850 mm×1500 mm in the x and y directions, respectively. Each parent sheet is flattened and a single retardation measurement made at points separated by 20 mm in the x direction and 100 mm in the y direction. The average of the 1674 retardation measurements is calculated for each sheet. Each parent sheet is cut into 4 sub-sheets at an OEM and the distortion reported for the x and y coordinates at each corner of each sub-sheet. The difference in the x coordinates between the two corners of each sub-sheet with y coordinate nearest to zero is calculated. This difference is referred to as pitch. Similar measurements are conducted for the two corners with y coordinate nearest to 1500. The difference in the y coordinates between the two corners of each sub-sheet with x coordinate nearest to zero was calculated and similar measurements are conducted for the two corners with y coordinate nearest to 1850. This results in 4 pitches per sub-sheet and 16 pitches for all the sub-sheets belonging to one parent sheet. The absolute value of the maximum pitch for each set of sub-sheets corresponding to a parent sheet is plotted versus the average retardation of the respective parent sheets and a linear fit is obtained using ordinary linear regression.

Figure 6:
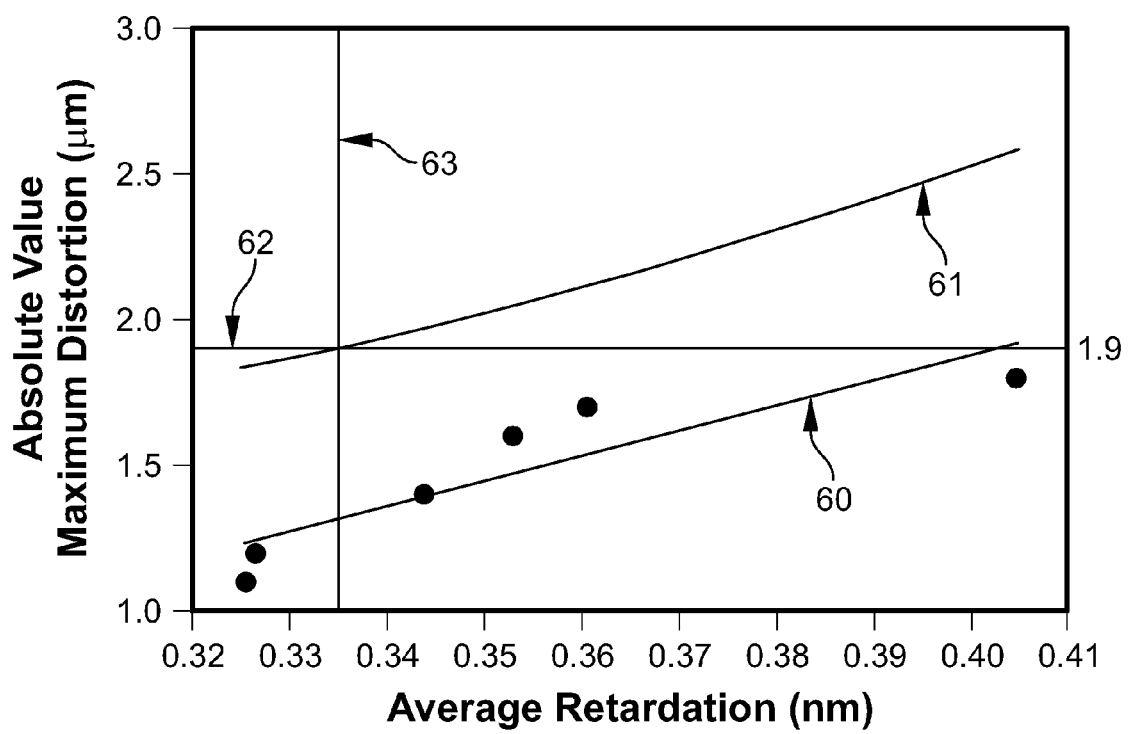
FIG. 6 is a plot illustrating a correlation between average retardation of a sample of parent glass sheets and an absolute value of the maximum distortion of sub-sheets cut from the parent sheets.

FIG. 6 shows the result where curve 60 is the line of means obtained from the regression fit. Curve 61 is the upper 95% statistical tolerance limit with confidence coefficient 0.95. Curve 62 takes the example where the manufacturing limit for distortion measured in the above manner is 1.9 μm. This distortion limit intersects the upper statistical tolerance limit at an average retardation of 0.335 nm. Therefore, if average retardation is controlled in manufacturing so that it does not exceed 0.335 nm, then 95% of manufactured sheets are expected have ≤1.9 μm distortion with 95% confidence. A target average retardation would be set in manufacturing so that the 3σ upper control limit is ≤0.335 nm and the glass manufacturing process is modified to form parent glass sheets with this target value of average retardation. Thus, it is possible to keep the distortion parameter (e.g., maximum distortion) below a specific value (e.g., 1.9 μm) with a predetermined probability (e.g., 95%) at a predetermined confidence level (e.g. 95%) by controlling the retardation parameter.

The average retardation is decreased by reducing any localized thermal gradients in the sheet that can cause localized stress fields, particularly parallel to the glass flow path. These temperature fields are reduced by machine design (design out thermal scarring and designing in discreet windings). In addition, the rate of cooling through the setting zone temperatures for all areas of the sheet is controlled to reduce the difference in expansion in one section of the sheet relative to another. This reduces bands of tension and compression and therefore retardation. The out of plane shape of the sheet is also reduced in the final product to reduce bands of tension and compression generated when the glass is forced flat due to gravity or vacuuming. The out of plane shape is reduced by rate of cooling through the setting zone and by mechanical devices to help hold the sheet in plane while being formed via, but not limited to, all-wheel drive, sheet guidance device, and robot tensioning and separation techniques.

Although the foregoing description has been presented in the context of a fusion downdraw method for making glass sheet, the present disclosure may be applied to other glass sheet forming processes, including but not limited to updraw and float methods.

It will be apparent to those skilled in the art that various modifications and variations can be made without departing from the spirit and scope of the claimed invention.

What is claimed is:

1. A method of reducing distortion in a glass sheet, comprising the steps of:
    forming a glass ribbon in a glass manufacturing process;
    separating a glass sheet from the glass ribbon, the glass sheet having a substantially flat surface;
    measuring a retardation value through the surface of the glass sheet at a plurality of locations of the glass sheet;
    determining an average retardation value of all of the measured retardation values;
    cutting the glass sheet into a plurality of sub-sheets;
    measuring a distortion of the sub-sheets;
    defining a distortion parameter indicative of the distortion of the sub-sheets;
    determining a correlation between the average retardation value and the distortion parameter such that a distortion parameter of sub-sheets of a subsequent glass sheet can be predicted based on the correlation; and
    modifying the glass manufacturing process such that an average retardation value of the subsequent glass sheet is adjusted to thereby reduce a distortion of the sub-sheets from the subsequent glass sheet based on the correlation.

2. The method of claim 1, wherein the distortion parameter is kept below a specific value with a predetermined probability.

3. The method of claim 1, wherein the step of measuring the distortion of the sub-sheets involves measuring an in-plane distortion defined as an offset of a first set of points along a plane of the sub-sheets prior to and after the step of cutting.

4. The method of claim 3, wherein the distortion parameter is equal to a maximum of the in-plane distortion measured at the first set of points.

5. The method of claim 1, further comprising:
    a step of flattening the glass sheet before the step of measuring the retardation value at the plurality of locations of the glass sheet; and
    a step of flattening each of the sub-sheets before the step of measuring the distortion.

6. A method of reducing distortion in a glass sheet, comprising the steps of:
    forming a glass ribbon in a glass manufacturing process;
    separating a glass sheet from the glass ribbon, the glass sheet having a substantially flat surface;
    measuring a retardation value through the surface of the glass sheet at a plurality of locations of the glass sheet;
    determining an average retardation value of all of the measured retardation values;
    cutting the glass sheet into a plurality of sub-sheets;
    measuring a distortion of the sub-sheets;
    defining a distortion parameter indicative of the distortion of the sub-sheets; and
    determining a correlation between the average retardation value and the distortion parameter such that a distortion parameter of sub-sheets of a subsequent glass sheet can be predicted based on the correlation.

7. The method of claim 6, further comprising a step of predicting a distortion parameter of sub-sheets of a subsequent glass sheet using the correlation between the average retardation value and the distortion parameter.

8. The method of claim 7, further comprising a step of modifying the glass manufacturing process such that an average retardation value of the subsequent glass sheet is adjusted to thereby reduce a distortion of the sub-sheets from the subsequent glass sheet based on the correlation.

9. The method of claim 8, wherein the distortion parameter is kept below a specific value with a predetermined probability.

10. The method of claim 6, wherein the step of determining involves formulating an equation using a least squares regression approach.

11. The method of claim 6, wherein the step of measuring the distortion of the sub-sheets involves measuring an in-plane distortion defined as an offset of a point along a plane of the sub-sheets prior to and after the step of cutting.

12. The method of claim 11, wherein the step of measuring the in-plane distortion of the sub-sheets involves measuring the in-plane distortion of a first set of points on the sub-sheets.

13. The method of claim 12, wherein the distortion parameter is equal to a maximum of the in-plane distortion measured at the first set of points.

14. The method of claim 13, further comprising a step of modifying the glass manufacturing process such that an average retardation value of the subsequent glass sheet is adjusted to thereby reduce a distortion of the sub-sheets from the subsequent glass sheet based on the correlation, and wherein the maximum of the in-plane distortion is kept below a specific value with a predetermined probability.

15. The method of claim 12, wherein the distortion parameter is equal to an average of the in-plane distortion measured at the first set of points.

16. The method of claim 15, further comprising a step of modifying the glass manufacturing process such that an average retardation value of the subsequent glass sheet is adjusted to thereby reduce a distortion of the sub-sheets from the subsequent glass sheet based on the correlation, and wherein the average of the in-plane distortion is kept below a specific value with a predetermined probability.

17. The method of claim 12, wherein corners of the sub-sheets define the first set of points.

18. The method of claim 11, wherein the point is a centroid of each of the sub-sheets.

* * * * *